(12) United States Patent
Peukert et al.

(10) Patent No.: US 9,808,295 B2
(45) Date of Patent: Nov. 7, 2017

(54) SPINE STABILIZATION SYSTEM, SET OF MEDICAL INSTRUMENTS AND MEDICAL APPARATUS FOR PARALLEL ALIGNMENT OF MEDICAL INSTRUMENTS

(71) Applicant: Aesculap AG, Tuttlingen (DE)

(72) Inventors: Andrea Peukert, Tuttlingen (DE); Fabian Hoefer, Tuttlingen (DE)

(73) Assignee: Aesculap AG (DE)

( * ) Notice: Subject to any disclaimer, the term of this patent is extended or adjusted under 35 U.S.C. 154(b) by 248 days.

(21) Appl. No.: 14/507,985

(22) Filed: Oct. 7, 2014

(65) Prior Publication Data
US 2015/0112399 A1    Apr. 23, 2015

(30) Foreign Application Priority Data
Oct. 23, 2013    (DE) ......................... 10 2013 111 683

(51) Int. Cl.
*A61B 17/88*    (2006.01)
*A61B 17/70*    (2006.01)

(52) U.S. Cl.
CPC ........ *A61B 17/7074* (2013.01); *A61B 17/708* (2013.01)

(58) Field of Classification Search
CPC ............ A61B 17/7014; A61B 17/7086; A61B 2017/681; A61B 17/7083; A61B 17/7085; A61B 17/025
USPC ......................... 606/86 A, 250–279, 99, 86 R
See application file for complete search history.

(56) References Cited

U.S. PATENT DOCUMENTS

| 7,892,238 | B2 | 2/2011 | DiPoto et al. | |
| 7,951,175 | B2 | 5/2011 | Chao et al. | |
| 2006/0200132 | A1* | 9/2006 | Chao | A61B 17/708 606/86 A |
| 2007/0213716 | A1* | 9/2007 | Lenke | A61B 17/025 606/264 |
| 2008/0045956 | A1 | 2/2008 | Songer | |

(Continued)

FOREIGN PATENT DOCUMENTS

| EP | 2066249 B1 | 7/2010 |
| EP | 2255739 A1 | 12/2010 |
| WO | WO 2009/114422 A2 | 9/2009 |

OTHER PUBLICATIONS

German Search Report with Partial Translation issued in related German Application No. 10 2013 111 683.3, dated Mar. 28, 2014.

*Primary Examiner* — Eduardo C Robert
*Assistant Examiner* — Tara R Carter
(74) *Attorney, Agent, or Firm* — RatnerPrestia

(57) ABSTRACT

A medical apparatus for parallel alignment of at least two medical instruments for holding and manipulating a surgical fastening element is described. The fastening element includes a fastening part and a holding part for a connection element, the holding part being movably mounted relative to the fastening part in a mounting position. The medical instruments have a distal end couplable to the fastening element. The apparatus includes at least two coupling devices, each defining a coupling longitudinal axis, for temporary coupling with proximal ends of the at least two medical instruments, wherein the apparatus comprises a frame, wherein the coupling longitudinal axes of the at least two coupling devices are alignable parallel to one another. Improved sets of medical instruments and improved spine stabilization systems are also described.

24 Claims, 15 Drawing Sheets

(56) References Cited

U.S. PATENT DOCUMENTS

Figure 1:
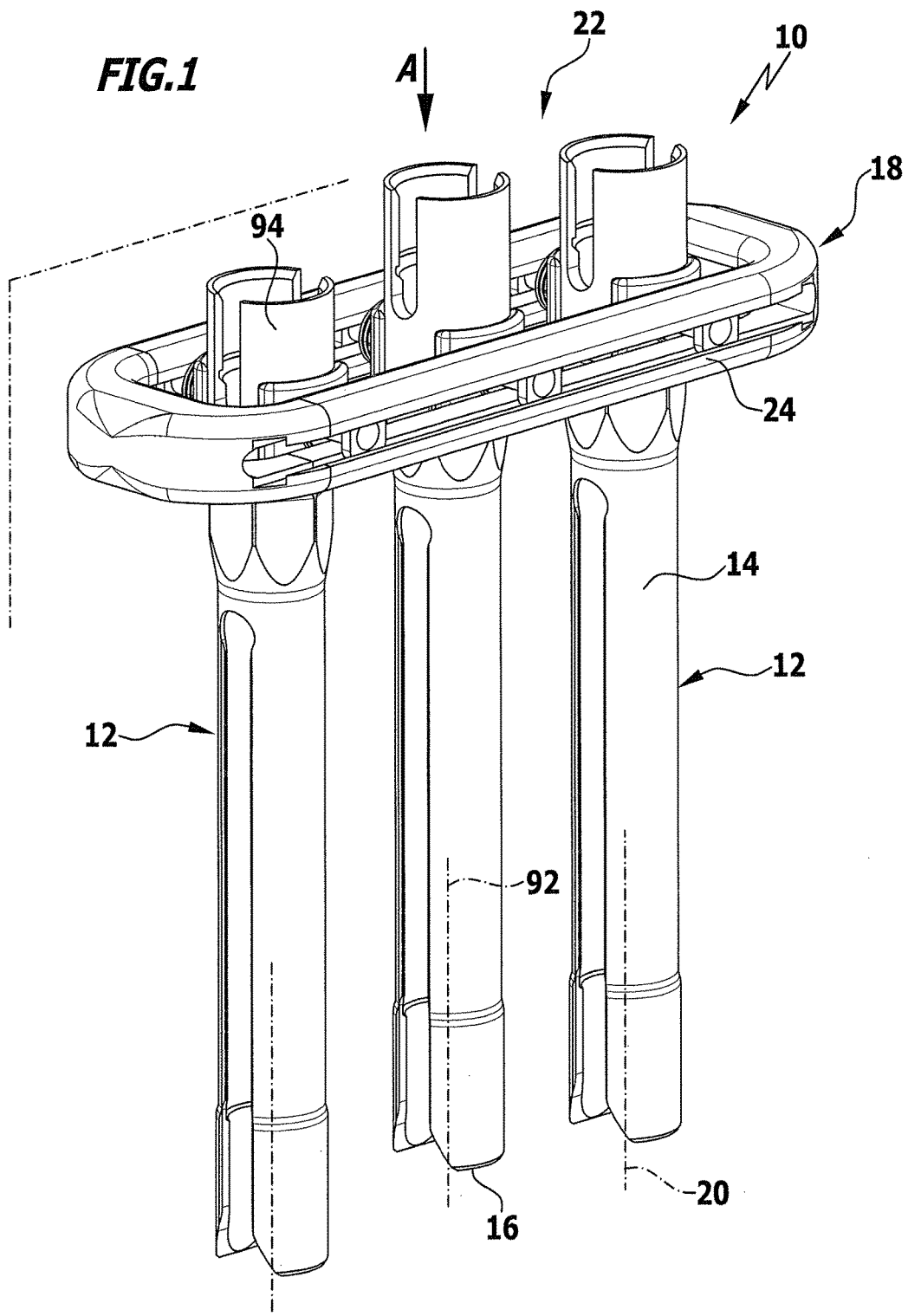

| | | |
|---|---|---|
| 2008/0172062 A1 | 7/2008 | Donahue et al. |
| 2011/0077689 A1 | 3/2011 | Mickiewicz |
| 2011/0106082 A1 | 5/2011 | Kave et al. |
| 2011/0196426 A1 | 8/2011 | Peukert et al. |
| 2013/0211453 A1* | 8/2013 | Lenke .................. A61B 17/708 606/250 |

* cited by examiner

SPINE STABILIZATION SYSTEM, SET OF MEDICAL INSTRUMENTS AND MEDICAL APPARATUS FOR PARALLEL ALIGNMENT OF MEDICAL INSTRUMENTS

CROSS-REFERENCE TO RELATED APPLICATIONS

The present disclosure relates to the subject matter disclosed in, and claims the benefit of priority of, German patent application number 10 2013 111 683.3, filed Oct. 23, 2013, which is incorporated by reference herein in its entirety and for all purposes.

FIELD OF THE INVENTION

The present invention relates to a medical apparatus for parallel alignment of at least two medical instruments generally, and more specifically to a medical apparatus for parallel alignment of at least two medical instruments, defining an instrument longitudinal axis, for holding and manipulating a surgical fastening element, which fastening element comprises a fastening part and a holding part for a connection element, the holding part being mounted movably relative to the fastening part in a mounting position, which medical instruments have a distal end couplable to the fastening element, which apparatus comprises at least two coupling devices, each defining a coupling longitudinal axis, for temporary coupling with proximal ends of the at least two medical instruments.

The present invention further relates to a sets of medical instruments for implanting a spine stabilisation system generally, and more specifically to a set of medical instruments for implanting a spine stabilisation system, which set of medical instruments comprises at least two medical instruments for holding and manipulating a surgical fastening element, which fastening element comprises a fastening part and a holding part for a connection element, the holding part being mounted movably relative to the fastening part in a mounting position, which medical instruments have a proximal end and a distal end couplable to the fastening element.

And finally the present invention also relates to a spine stabilisation systems generally, and more specifically to a spine stabilisation system comprising at least two surgical fastening elements and at least one connection element, at least one of the at least two surgical fastening elements comprising a fastening part, a holding part with a connection element receptacle and a fixing element securable to the holding part for securing the connection element in the connection element receptacle.

BACKGROUND OF THE INVENTION

A spine stabilisation system and medical instruments of the type described for holding and manipulating surgical fastening elements are known for example from US 2011/0196426 A1, which also discloses a medical apparatus of the above-described type. This serves to connect together the instruments coupled with surgical fastening elements in the form of polyaxial pedicle screws, in order to orient the holding parts of the fastening elements in a defined manner relative to one another. The instruments are used in particular for minimally invasive securing of the spine stabilisation system to a human or animal spine. Since, in the case of minimally invasive use of the instruments, the distal ends thereof, coupled with the holding parts of the fastening elements, are not visible to a surgeon, but the surgeon has to insert connection elements, for example connecting rods, into corresponding connection element receptacles on the holding parts, in order to secure them thereto, such that the bone screws are held in a defined relative position to one another, it is desirable to know the orientation of the connection element receptacles, even if these are not directly visible. The purpose of the medical apparatus is to simplify insertion of the connection element. In US 2011/0196426 A1 such an apparatus comprises individual members, which are coupled directly together. Each member of the apparatus forms a coupling device, which is in each case temporarily couplable to an instrument.

A disadvantage of the known medical apparatus is in particular that it is awkward to couple to the medical instruments, i.e. in particular such coupling takes a lot of time. Furthermore, parallel alignment of the longitudinal axes of the medical instruments on insertion of the known apparatus cannot be guaranteed with absolute reliability.

SUMMARY OF THE INVENTION

In a first aspect of the invention, a medical apparatus is provided for parallel alignment of at least two medical instruments, defining an instrument longitudinal axis, for holding and manipulating a surgical fastening element. Said fastening element comprises a fastening part and a holding part for a connection element. The holding part is mounted movably relative to the fastening part in a mounting position. Said medical instruments have a distal end couplable to the fastening element. Said apparatus comprises at least two coupling devices, each defining a coupling longitudinal axis, for temporary coupling with proximal ends of the at least two medical instruments. The apparatus comprises a frame. The coupling longitudinal axes of the at least two coupling devices are alignable parallel to one another. In a mounting position the at least two coupling devices are held in such a way as to be movable relative to one another and on the frame and in an alignment position they are held immovably relative to one another and on the frame.

In a second aspect of the invention, a set of medical instruments is provided for implanting a spine stabilisation system. Said set of medical instruments comprises at least two medical instruments for holding and manipulating a surgical fastening element. Said fastening element comprises a fastening part and a holding part for a connection element. The holding part is mounted movably relative to the fastening part in a mounting position. Said medical instruments have a proximal end and a distal end couplable to the fastening element. Said set of medical instruments further comprises a medical apparatus for parallel alignment of said at least two medical instruments, defining an instrument longitudinal axis. Said apparatus comprises at least two coupling devices, each defining a coupling longitudinal axis, for temporary coupling with proximal ends of the at least two medical instruments. The apparatus comprises a frame. The coupling longitudinal axes of the at least two coupling devices are alignable parallel to one another. In a mounting position the at least two coupling devices are held in such a way as to be movable relative to one another and on the frame and in an alignment position they are held immovably relative to one another and on the frame.

In a third aspect of the invention, a spine stabilisation system comprises at least two surgical fastening elements and at least one connection element. At least one of the at least two surgical fastening elements comprises a fastening part, a holding part with a connection element receptacle and a fixing element securable to the holding part for securing the connection element in the connection element receptacle. Said system further comprises a medical apparatus for parallel alignment of at least two medical instruments, defining an instrument longitudinal axis, for holding and manipulating a surgical fastening element. Said fastening elements comprise a fastening part and a holding part for a connection element. The holding part is mounted movably relative to the fastening part in a mounting position. Said medical instruments have a distal end couplable to the fastening element. Said apparatus comprises at least two coupling devices, each defining a coupling longitudinal axis, for temporary coupling with proximal ends of the at least two medical instruments. The apparatus comprises a frame. The coupling longitudinal axes of the at least two coupling devices are alignable parallel to one another. In a mounting position the at least two coupling devices are held in such a way as to be movable relative to one another and on the frame and in an alignment position they are held immovably relative to one another and on the frame. Alternatively, the spine stabilsations system comprises a set of medical instruments in accordance with the invention outlined above.

BRIEF DESCRIPTION OF THE DRAWING FIGURES

Figure 2:
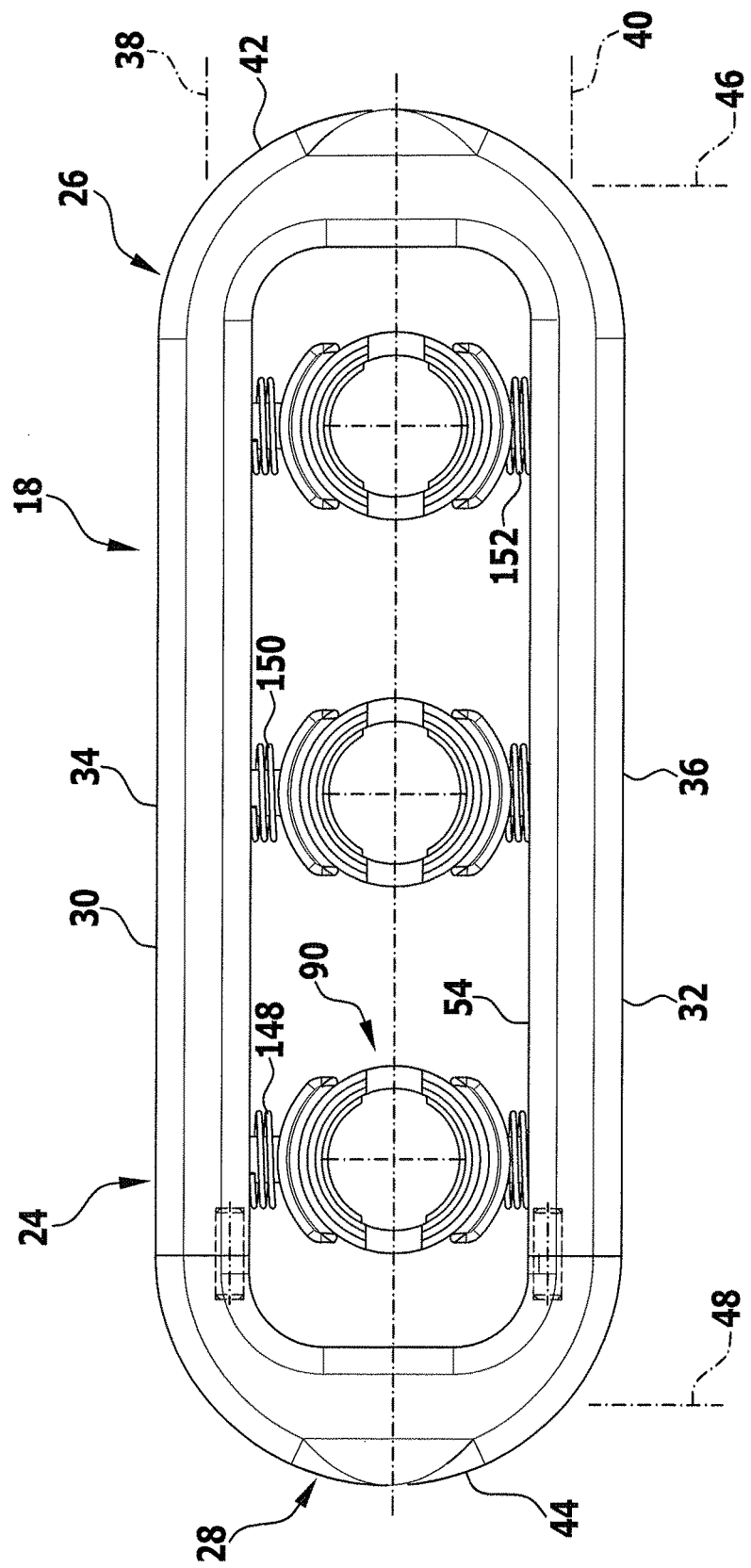
Figure 3:
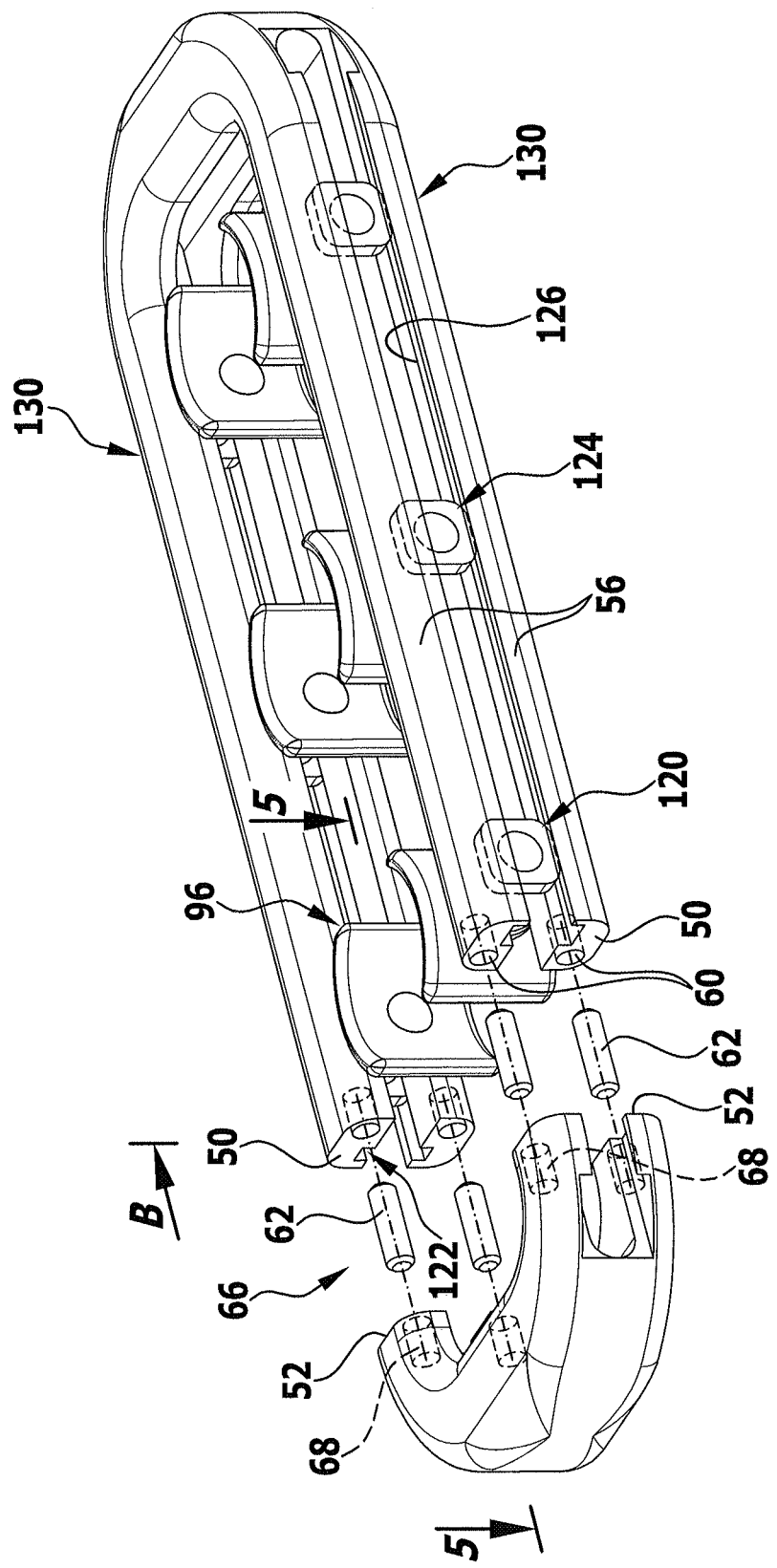
Figure 4:
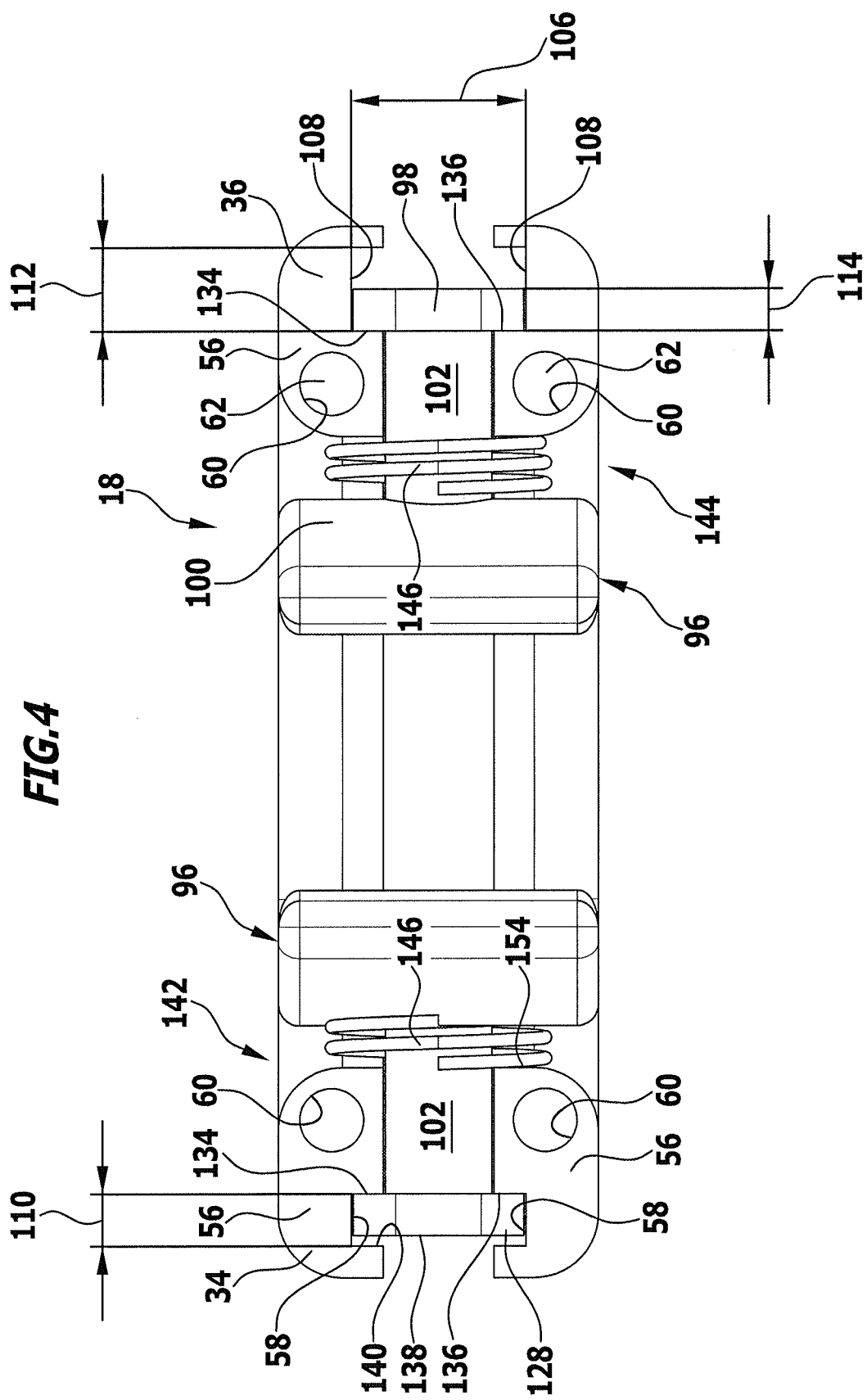
Figure 5:
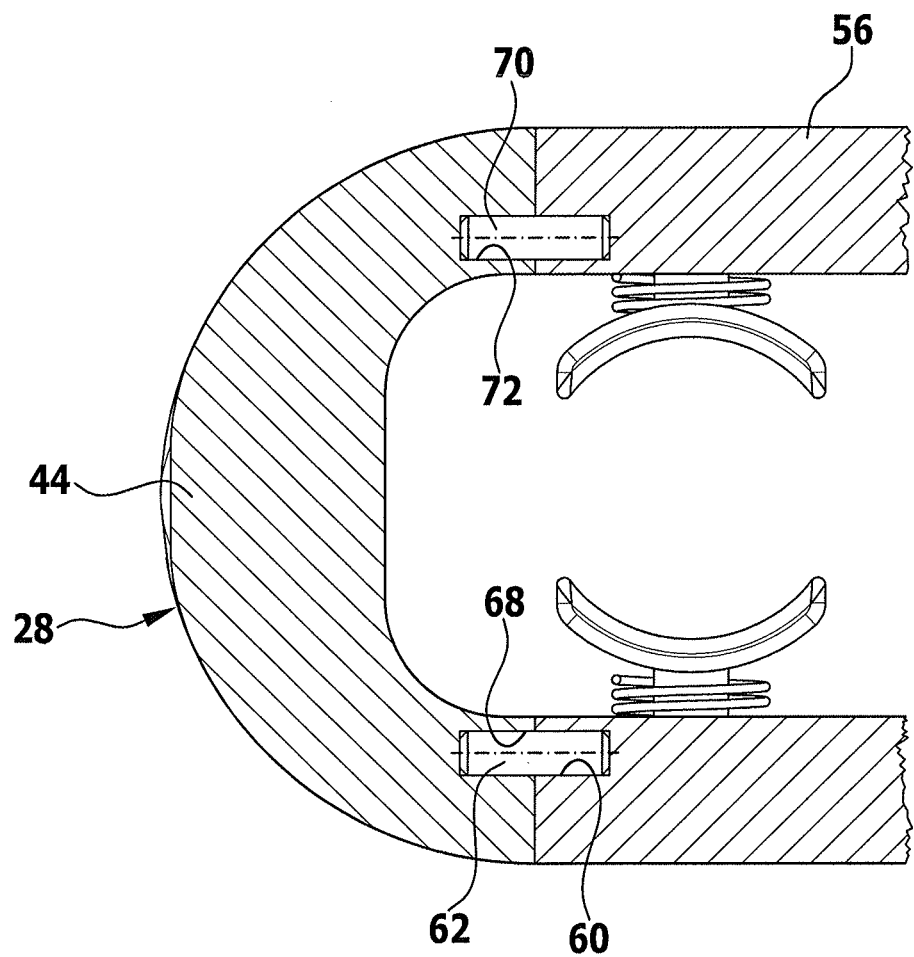
Figure 6:
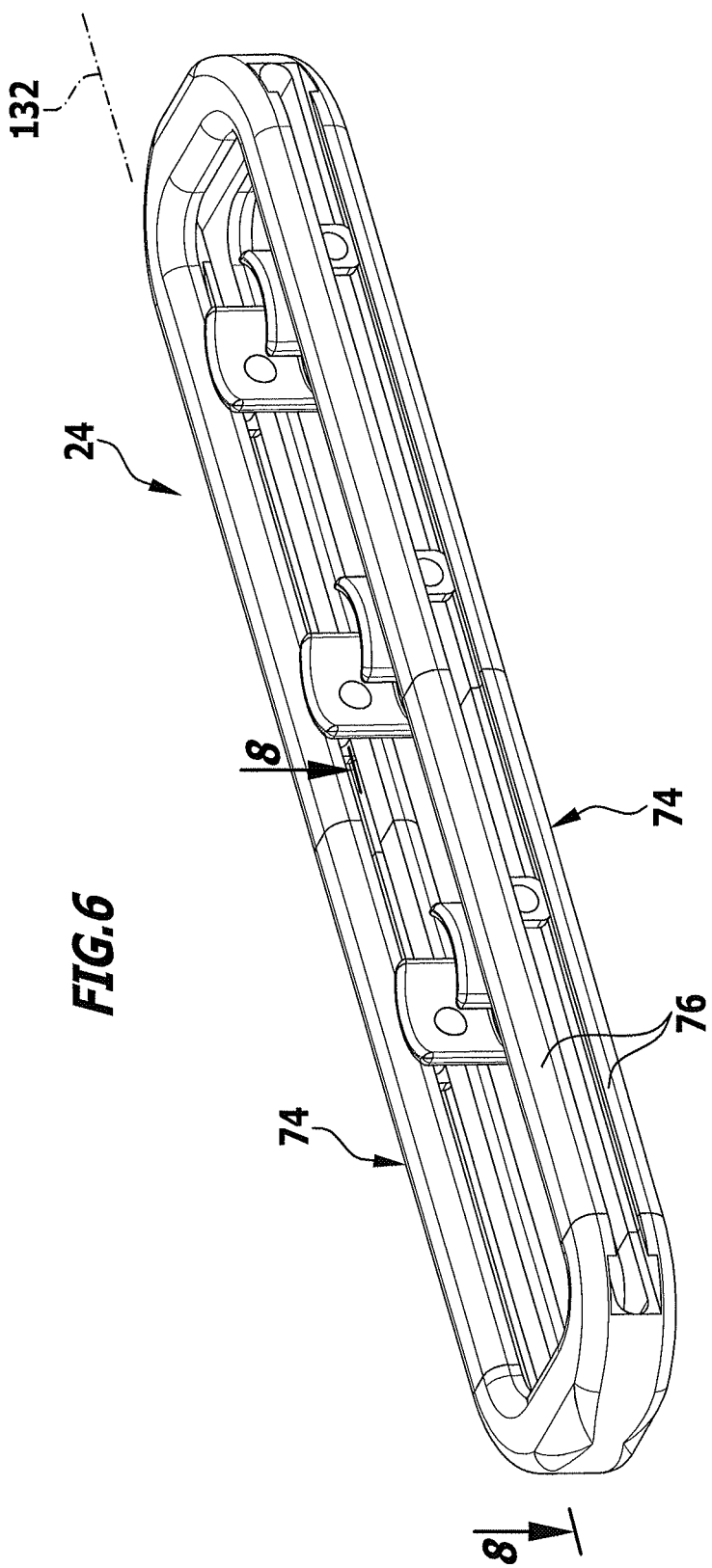
Figure 7:
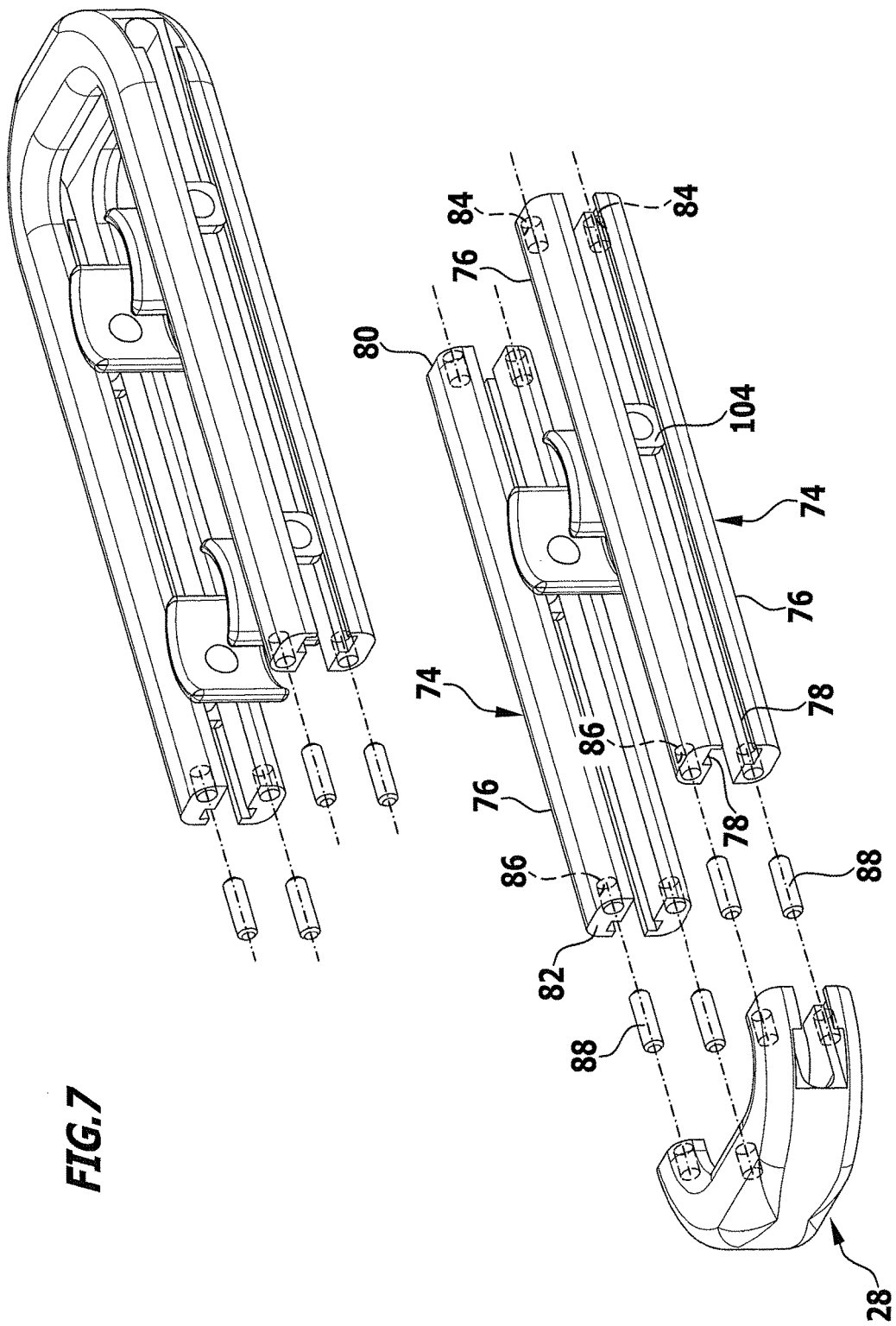
Figure 8:
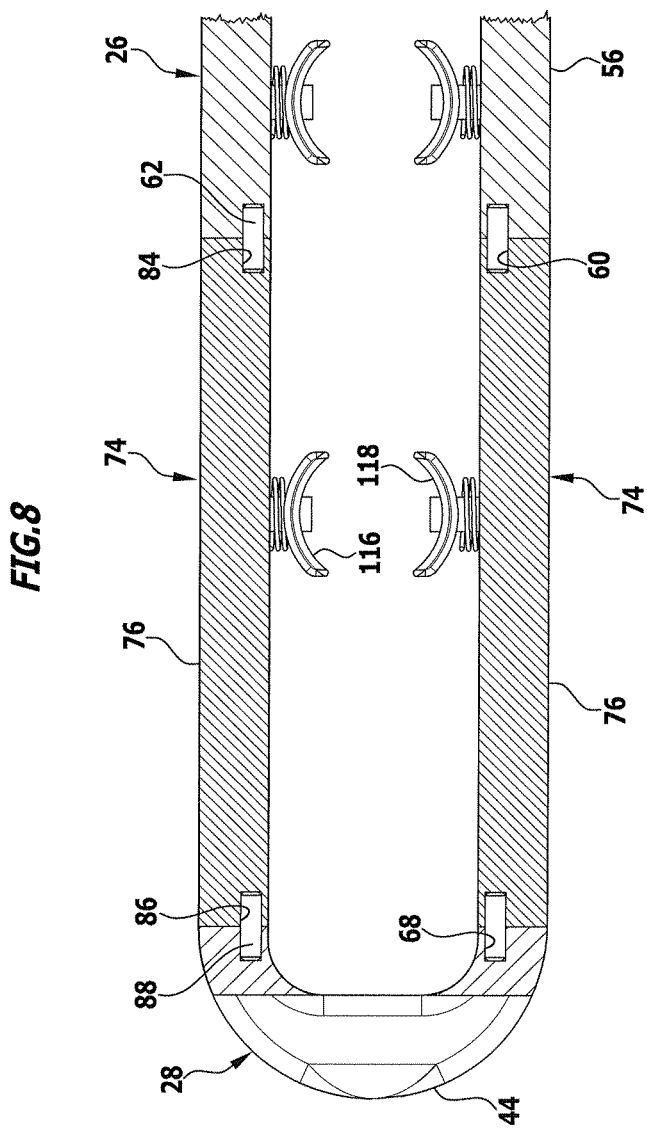
Figure 9:
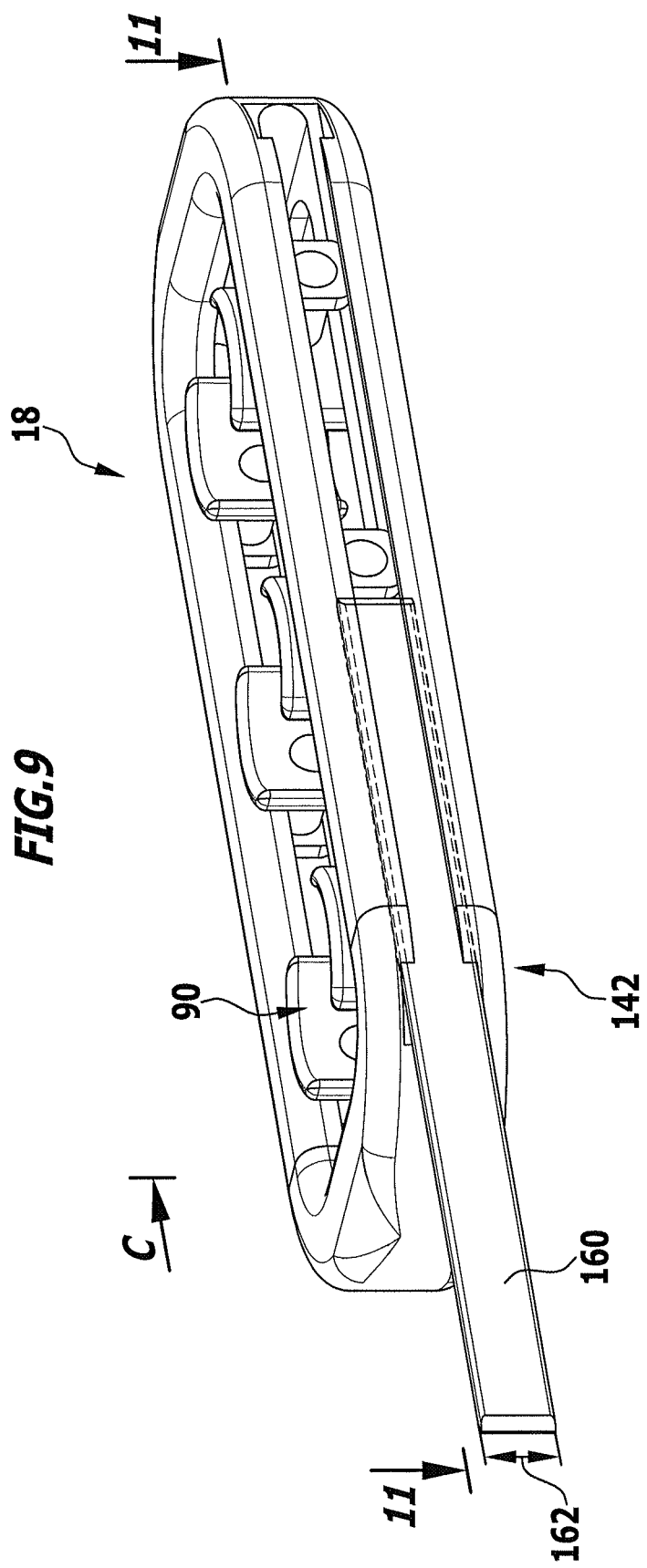
Figure 10:
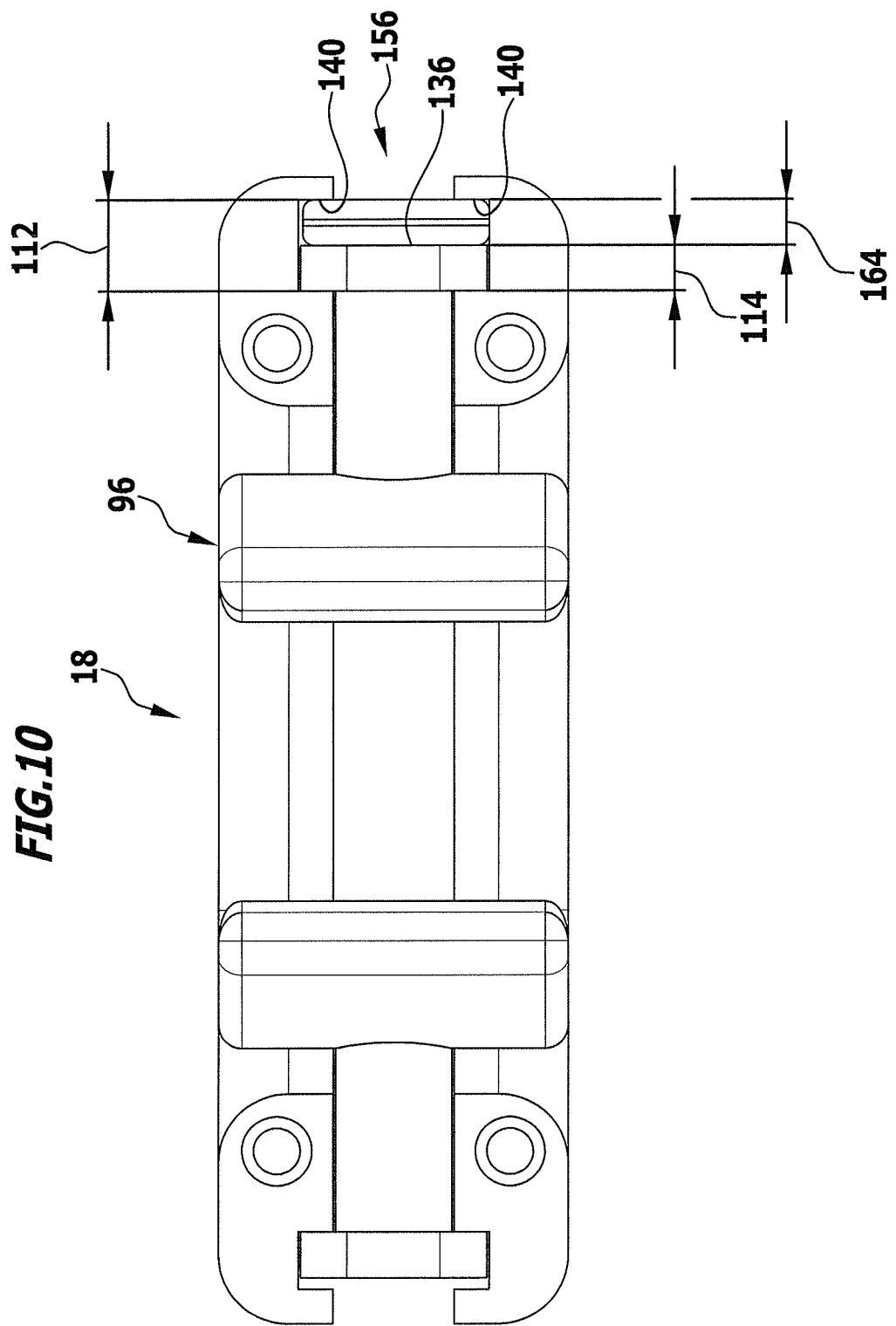
Figure 11:
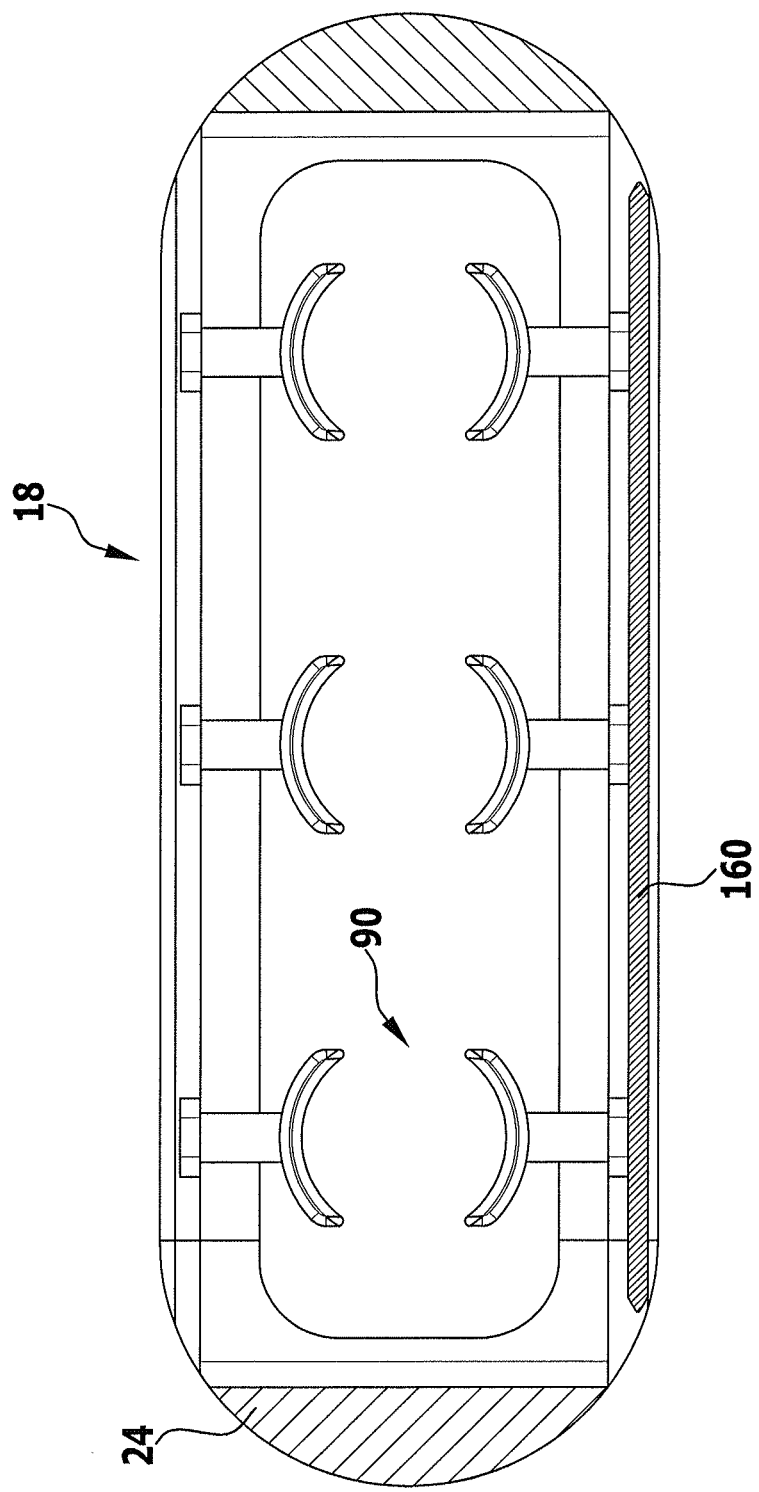
Figure 12:
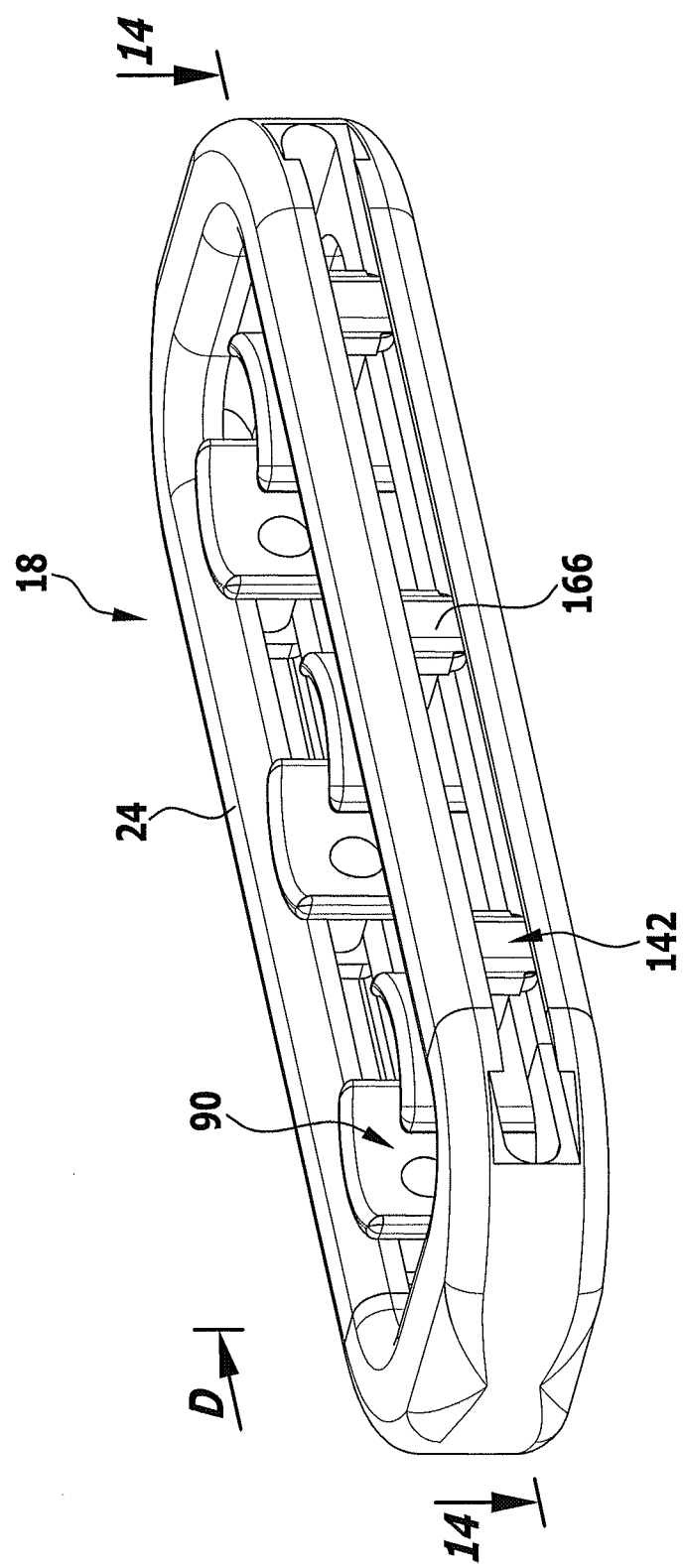
Figure 13:
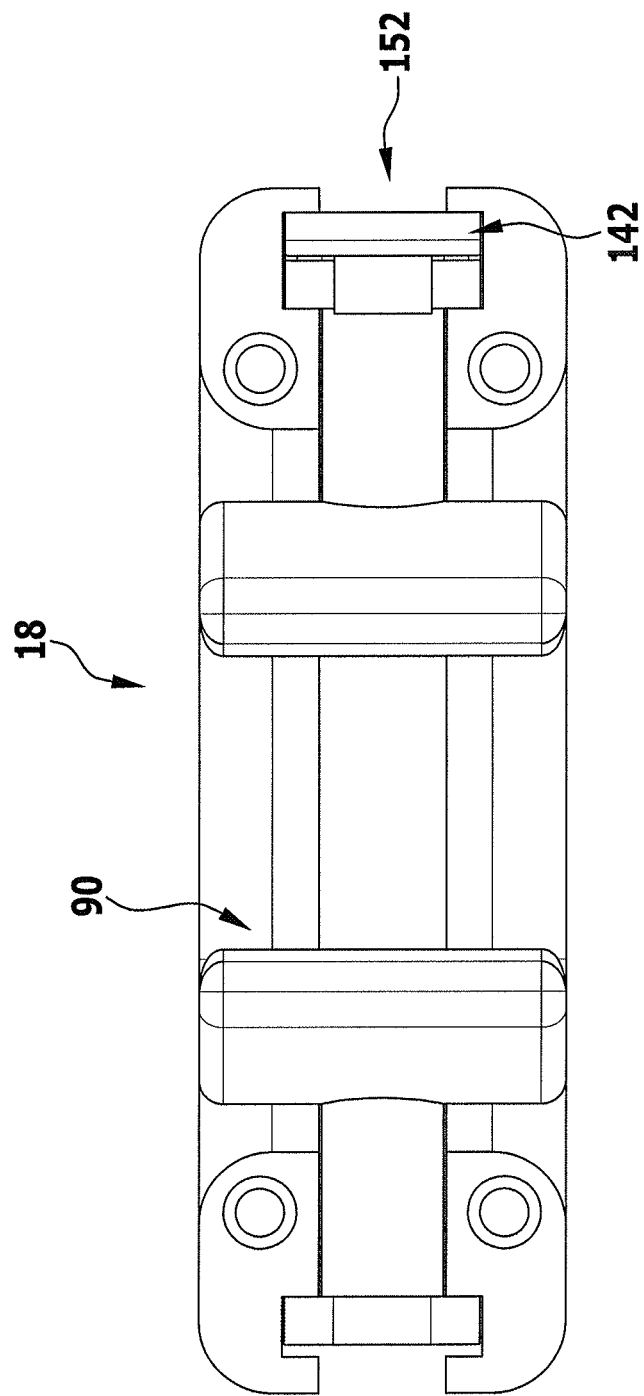
Figure 14:
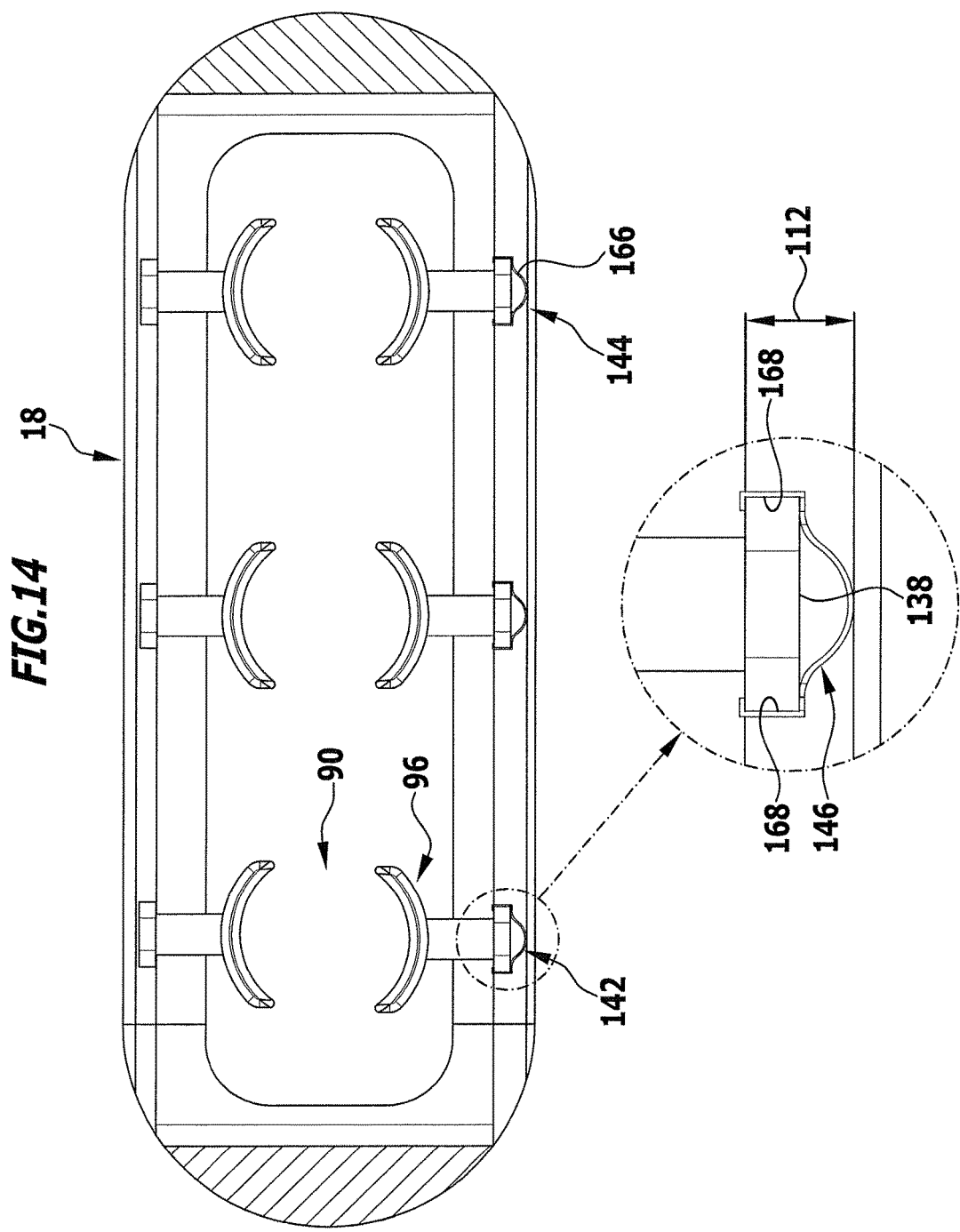

The foregoing summary and the following description may be better understood in conjunction with the drawing figures, of which:

FIG. 1: is a schematic perspective overall view of a first exemplary embodiment of a medical apparatus with three medical instruments oriented parallel to one another thereon;

FIG. 2: is a view of the arrangement of FIG. 1 in the direction of arrow A;

FIG. 3: is a schematic perspective view of the medical apparatus of FIG. 2 on joining together of frame longitudinal portions with a frame cross-portion;

FIG. 4: is a view of the arrangement of FIG. 3 in the direction of arrow B;

FIG. 5: is a sectional view along line 5-5 in FIG. 3;

FIG. 6: is a schematic perspective representation of the apparatus of FIG. 3 extended by two frame portion extensions;

FIG. 7: is a schematic perspective exploded representation of the arrangement of FIG. 6;

FIG. 8: is a sectional view along line 8-8 in FIG. 6;

FIG. 9: shows a schematic perspective arrangement of a second exemplary embodiment of a medical apparatus;

FIG. 10: is a view of the arrangement of FIG. 9 in the direction of arrow C;

FIG. 11: is a sectional view along line 11-11 in FIG. 9;

FIG. 12: is a schematic perspective representation of a third exemplary embodiment of a medical apparatus;

FIG. 13: is a view of the arrangement of FIG. 12 in the direction of arrow D;

FIG. 14: is a sectional view along line 14-14 in FIG. 12; and

Figure 15:
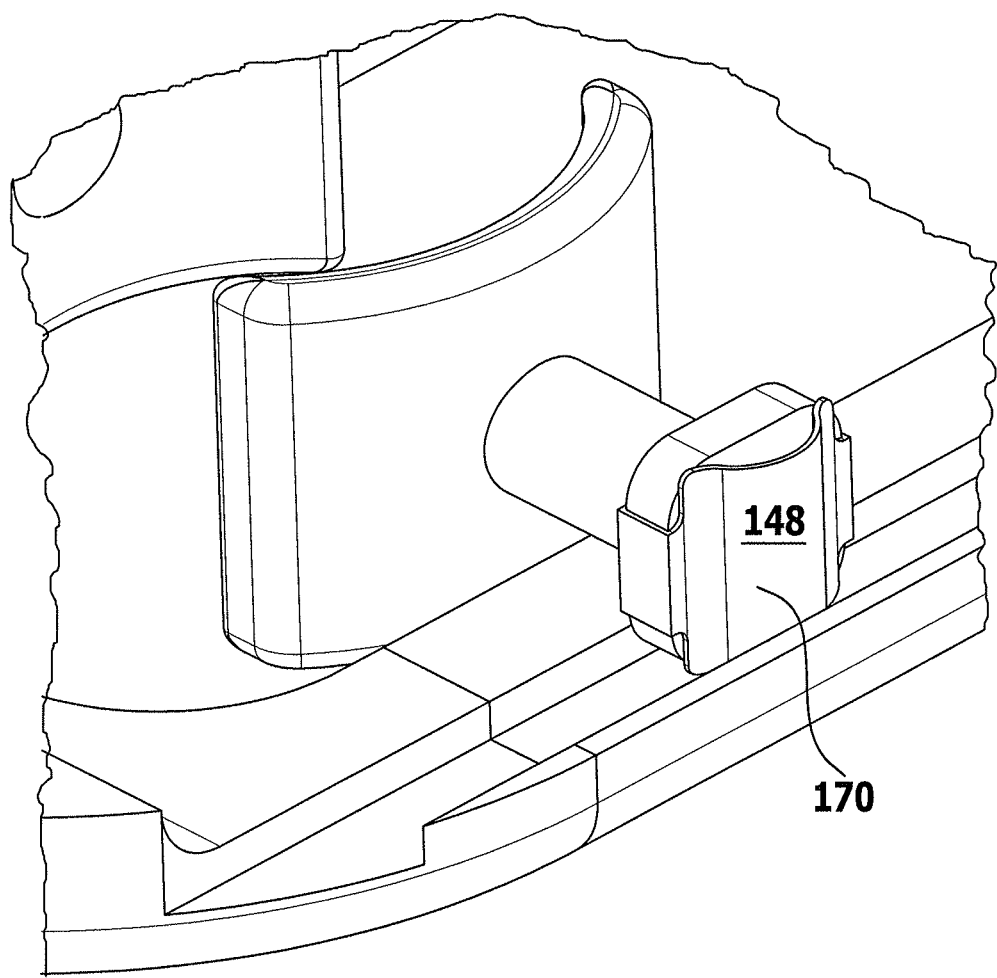

FIG. 15: is a schematic, enlarged, perspective view of a coupling member of the arrangement of FIG. 12 with a clamping member in the form of a leaf spring.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical apparatus for parallel alignment of at least two medical instruments, defining an instrument longitudinal axis, for holding and manipulating a surgical fastening element, which fastening element comprises a fastening part and a holding part for a connection element, the holding part being mounted movably relative to the fastening part in a mounting position, which medical instruments have a distal end couplable to the fastening element, which apparatus comprises at least two coupling devices, each defining a coupling longitudinal axis, for temporary coupling with proximal ends of the at least two medical instruments, wherein the apparatus comprises a frame, wherein the coupling longitudinal axes of the at least two coupling devices are alignable parallel to one another, wherein in a mounting position the at least two coupling devices are held in such a way as to be movable relative to one another and on the frame and wherein in an alignment position they are held immovably relative to one another and on the frame.

The medical apparatus further developed according to the invention makes it possible, in particular, to align and hold medical instruments of the above-described type in a defined and reliably parallel manner. In particular, it is possible to arrange two or more coupling devices on the frame, specifically as a function of the number of medical instruments used to hold and manipulate the fastening elements. Unlike with the medical apparatus known from US 2011/0196426 A1, the spacings between the coupling devices may vary, in particular in the mounting position, and may optionally be secured in the alignment position in such a way that movement of the medical instruments is impossible or is possible only with difficulty. Optimum parallel alignment of the instruments with the medical apparatus allows precise determination of a length and orientation or curvature of the connection element which is to be secured on the implanted fastening elements in the connection element receptacles thereof.

It is favourable for each of the coupling devices to comprise at least two coupling members, which are held in the mounting position so as to be movable relative to one another and on the frame and which are held in the alignment position so as to be immovable relative to one another and on the frame. With coupling devices configured in this way, medical instruments may be held in defined and secure manner in the alignment position. Applying the medical apparatus to two or more medical instruments is particularly simple, since the at least two coupling members, in particular there may be just two, are movable relative to one another in the mounting position. For example they may be movable away from one another, to simplify insertion of a medical instrument between them. In particular, in this way it is possible with the medical apparatus to take hold of all the medical instruments in one step and align them parallel to one another.

To achieve optimum adaptation and alignment of the instruments, it is advantageous for each coupling member to have an instrument application face, which is conformed to an external contour of the medical instrument in the region of the proximal end thereof. This makes it possible to prevent tilting or undesired inclination of the instrument relative to the coupling device, which may in particular lead to non-parallel orientation of the at least two instruments held on the medical apparatus. The instrument application face favourably extends in a direction parallel to the instrument longitudinal axis to a length which corresponds for instance to half the width of the instrument application face transversely of the instrument longitudinal axis. For particularly good and precise alignment of the instruments, the greater the extent of the instrument application face parallel to the instrument longitudinal axis relative to the width of the instrument application face, the more advantageous it is.

In particular, it is advantageous for the instrument application face to take the form of a hollow-cylindrical wall face portion. Such a hollow-cylindrical wall face portion, which preferably defines an internal diameter which corresponds to an external diameter of the instrument to be held and oriented, may be used in particular for large-area application to a cylindrical outer face of the instrument.

Medical instruments may be simply oriented parallel to one another if the frame comprises a first and a second frame portion, which extend parallel to one another. In particular, two pairs of frame portions extending parallel to one another may also be provided. These may in particular form portions of the frame extending lengthwise and transversely of one another.

It is favourable for the frame to comprise at least two frame cross-portions, which extend parallel or substantially parallel to one another, for the first and second frame portions to form frame longitudinal portions and for the at least two frame cross-portions to connect together the frame longitudinal portions, in particular free ends thereof. In this way, a rectangular or substantially rectangular frame may in particular be formed. Preferably, spacings of the frame longitudinal portions are conformed to cross-sections of the instruments to be aligned, such that these may be introduced between the frame longitudinal portions. In this way, in particular all the medical instruments may be held and aligned within the free face of the frame bordered by the frame longitudinal portions and frame cross-portions. The frame cross-portions may in particular virtually close the frame. They may optionally be configured to hold coupling members. However, they may also serve merely to connect the frame longitudinal portions and to stabilise the frame.

It is advantageous for the at least two frame cross-portions to define frame cross-portion longitudinal axes, which extend transversely of, in particular perpendicularly to, frame longitudinal portion longitudinal axes of the at least two frame longitudinal portions. In particular in the case of rectangular arrangement of the frame cross-portion longitudinal axes and the frame longitudinal portion longitudinal axes, an overall rectangular or substantially rectangular frame may be formed.

According to a further preferred embodiment of the invention, provision may be made for the frame to be of modular construction and to comprise at least one frame portion extension for extending the first and second frame portions and for the at least one frame portion extension to be detachably connectable to the first and/or second frame portion. The frame may be enlarged with one or indeed two frame portion extensions. In particular, the frame portion extensions may be similar to the frame portions in construction, in order to arrange coupling devices or the coupling members thereof thereon. Such a modular frame therefore makes it possible to enlarge the frame as required, in order to orient parallel to one another the number of medical instruments needed for a surgical operation. The frame may thus be individually conformed in size to the respective requirement, such that it only minimally impairs access and the view of the operation site for the surgeon.

It is easy to construct the frame in modular manner if it comprises a frame portion connection device for detachable connection of parts of the frame forming the latter. The frame portion connection device in particular makes it possible to connect frame longitudinal portions with frame cross-portions and optionally also frame portion extensions temporarily to one another, in order in this way simply and reliably to form a frame of the required size. The frame portion connection device may in particular take the form of a latching or snap-fit connection, which has interacting latching or snap-fit members on the parts of the frame to be connected together.

It is favourable for the frame portion connection device to comprise first and second interacting frame portion connection members, which are engaged in force- and/or positively-locking manner with one another in a frame connection position. In particular, first and second frame portion connection members may be arranged or formed on the portions of the frame to be connected with one another. The frame portion connection members may in particular take the form of latching or snap-fit members, which allow force- and/or positively-locking connections.

Parts of the frame may be coupled together particularly simply if the first and second interacting frame portion connection members take the form of frame portion connecting projections and corresponding frame portion connecting receptacles. These may be simply brought together if the frame portion connection members define longitudinal axes which extend for example parallel to frame longitudinal portion longitudinal axes or frame cross-portion longitudinal axes.

Preferably, the first and second interacting frame portion connection members are arranged or formed on a frame portion, on a frame longitudinal portion, on a frame cross-portion and/or on a frame portion extension. Ideally, the frame portion connection members are arranged in such a way that the stated parts may be connected together substantially as desired. Preferably, the frame portion connection members are each connected nondetachably with one of the stated parts, such that the number of free parts, in particular of small parts, may be minimised. This minimises the risk of parts of the frame being lost in the region of the operation site.

Parts forming the frame, in particular the first and second frame portions, are favourably of one-piece construction. In this way, the number of parts forming the frame can be minimised. In particular, it is feasible to construct the frame from just two parts, for example a unit of two frame longitudinal portions, which are connected permanently via a frame cross-portion, or for example from four parts, two frame longitudinal portions and two frame cross-portions detachably connectable therewith. To enlarge the frame, two frame portion extensions may then for example additionally extend the two frame longitudinal portions. The frame portion extensions may also take the form of a one-piece unit, for example connected via a crosspiece, such that here too the parts may if necessary be simply joined together and the frame simply expanded.

Advantageously, the apparatus comprises a connection device for movable connection of the coupling members with the frame. Such a connection device makes it possible to position the coupling members and thus the coupling devices virtually as desired on the frame, in order in this way to conform the frame and the position of the coupling devices arranged thereon as a function of the respective operative situation to the medical instruments which need to be oriented.

The connection device may be simply configured if it comprises at least one first connection element and at least one second connection element interacting with the at least one first connection element, if the frame comprises the at least one first connection element and if the at least one second connection element is arranged or formed on the coupling member. Such a configuration in particular makes it possible to arrange the coupling member directly on the frame or one of the parts forming the latter.

It is favourable for the at least one first connection element to take the form of a connecting receptacle and for the at least one second connection element to take the form of a connecting projection. Such connection elements may be brought simply into force-locking or positive engagement with one another, such that the coupling members may be held in simple and defined manner on the frame. In particular, they may also be simply configured in such a way that rotation thereof may be prevented, for example by appropriate selection of their shape. In particular, they may have cross-sectional areas and shapes which deviate from rotational symmetry, such that rotation of the coupling members relative to the frame is impossible.

In the mounting position the connecting projection is favourably displaceable in or on the connecting receptacle. This makes it possible, in particular, simply to displace the coupling member relative to the frame in the mounting position, in order to position it precisely where it is needed for receiving part of the medical instrument to be aligned.

The frame can be simply configured if the connecting receptacle is part of a guide rail or guide groove. In this way, it is in particular sufficient for just one guide rail or guide groove to be formed or arranged on a frame portion. This makes it possible in particular to arrange two or more coupling members therein, to displace them in the mounting position and to fix them in the alignment position.

To be able to align two coupling members simply, quickly and reliably parallel to one another to form a coupling device, it is advantageous for the connection device to comprise two connecting receptacles extending parallel to one another.

To simplify accommodation of a medical instrument in a coupling device, it is advantageous for the two coupling members defining a coupling device to be movable relative to one another in a direction transverse to a longitudinal direction defined by the at least one first connection element away from one another on changeover from the alignment position to the mounting position and towards one another on changeover from the mounting position to the alignment position. In other words, in this way in particular a distance between the coupling members may be enlarged on changeover from the alignment position to the mounting position, such that for example a sleeve-type instrument portion of the medical instrument to be aligned may be introduced between the coupling members.

The coupling device preferably comprises a locking device for securing a position and/or alignment of the coupling members in the alignment position. In this way, the locking device makes it possible in particular to prevent the coupling members from moving relative to one another in an undesired manner in the alignment position. Thus, parallel alignment of the instruments held with the apparatus may be ensured.

The locking device favourably comprises a clamping or blocking device for clamping securing of the coupling members in the alignment position on the frame or for blocking movement thereof relative to one another. With the clamping or blocking device, the coupling members may thus be secured relative to one another and/or relative to the frame in particular in the alignment position.

It is favourable for the clamping device to comprise at least one clamping member for clamping securing of the coupling members on the frame in the alignment position. The at least one clamping member may in particular take the form of a resilient element or indeed the form of a non-resilient body, which clampingly blocks one or more coupling members on the frame or a part thereof. In particular, the clamping member may also exert a force which depends on whether the coupling member is in the mounting position or in the alignment position.

The at least one clamping member favourably takes the form of a spring element. In this way, the coupling member may for example be transferred from the alignment position into the mounting position against the action of the spring element, in order to move the coupling member relative to the frame.

The clamping device may be particularly simply constructed if the spring element takes the form of a leaf spring or helical spring.

According to a further preferred embodiment of the invention, provision may be made for at least one coupling member of each coupling device to be transferable from the alignment position into the mounting position against the action of the clamping member. The coupling member, for example a resilient element, in particular in the form of a spring element, may for example be arranged in such a way that it exerts a force on the coupling member such that, to transfer the coupling member from the alignment position into the mounting position, a force must be exerted against the action of the clamping member. This makes it possible in particular to prevent the coupling members from moving undesirably of their own accord relative to one another or relative to the frame.

It is advantageous for just one of the two coupling members of a coupling device to comprise a clamping member. This minimises the design and also the production and assembly effort required for the apparatus. Of course it is also possible to equip both coupling members of a coupling device with a clamping member.

Advantageously, the clamping member takes the form of a compression or tension member. The coupling member may thus be fixed to the frame in the alignment position in particular by compressive or pulling forces.

It is advantageous if at least one of the coupling members has a guide portion, a holding portion and a connecting member connecting the guide portion and the holding portion. In particular, the two coupling members of a coupling device may be constructed in this way. Through this configuration, the respective parts of the coupling member may be optimised in accordance with their task, for example also be made from different materials.

The apparatus can be formed particularly simply and compactly if the guide portion is or comprises the second connection element. It is thus in particular possible for the guide portion to be used not only to guide the coupling member on the frame but in particular also to connect said member with the frame.

It is advantageous for the guide portion to be configured for non-rotatable displacement on at least one first connection element. In particular, the guide portion may be configured in such a way that antitwist protection or non-rotatable displacement is possible, in particular in the mounting position. The non-rotatable configuration of the guide portion and of the first connection element makes it possible to prevent a longitudinal axis defined by the coupling device from being undesirably tilted and the instruments aligned on the apparatus thus from being tilted relative to one another.

It is favourable for the guide portion to be held in the connecting receptacle in such a way as to be displaceable parallel to the longitudinal direction. The coupling member may thus if required be displaced simply and reliably in the desired manner relative to the frame, in particular in the mounting position.

A coupling member may be simply secured to the frame in the alignment position if the clamping member is supported on the one hand on the holding portion and on the other hand on the connecting receptacle or on the one hand on the connecting receptacle and on the other hand on the guide portion. Where the clamping member is preferably supported depends in particular on the type of clamping member, i.e. on whether the latter takes the form of a compression member or a pulling member.

It may moreover be advantageous for the blocking device to comprise a blocking element which may be inserted into the connecting recess in the mounting position and in the alignment position is arranged between a side face of the guide portion facing away from the holding portion and an inner guide face of the connecting recess. The blocking element may for example take the form of a non-resilient or substantially non-resilient element, for example the form of a metal or plastics strip which may be inserted into a gap formed between the guide portion and the connecting recess in order in this way to prevent movement of the coupling member transversely of the longitudinal direction.

It is advantageous for the blocking element to be formed to block movement of at least two coupling members simultaneously. In particular, the entire apparatus may in this way be simply secured in the alignment position. In particular, it is conceivable to use a single blocking element, which is inserted into a guide groove or guide rail to prevent movement of the coupling members transversely of the longitudinal direction. This makes it possible to dispense fully with spring elements or resilient elements.

Further, the invention relates to a set of medical instruments for implanting a spine stabilisation system, which set of medical instruments comprises at least two medical instruments for holding and manipulating a surgical fastening element, which fastening element comprises a fastening part and a holding part for a connection element, the holding part being mounted movably relative to the fastening part in a mounting position, which medical instruments have a proximal end and a distal end couplable to the fastening element, further comprising a medical apparatus for parallel alignment of at least two medical instruments, defining an instrument longitudinal axis, for holding and manipulating a surgical fastening element, which fastening element comprises a fastening part and a holding part for a connection element, the holding part being mounted movably relative to the fastening part in a mounting position, which medical instruments have a distal end couplable to the fastening element, which apparatus comprises at least two coupling devices, each defining a coupling longitudinal axis, for temporary coupling with proximal ends of the at least two medical instruments, wherein the apparatus comprises a frame, wherein the coupling longitudinal axes of the at least two coupling devices are alignable parallel to one another, wherein in a mounting position the at least two coupling devices are held in such a way as to be movable relative to one another and on the frame and wherein in an alignment position they are held immovably relative to one another and on the frame.

The set of medical instruments then likewise exhibits the advantages described above in relation to preferred embodiments of the medical apparatus. It allows simple, reliable and precise implantation of a spine stabilisation system.

Moreover, the invention relates to a spine stabilisation system comprising at least two surgical fastening elements and at least one connection element, at least one of the at least two surgical fastening elements comprising a fastening part, a holding part with a connection element receptacle and a fixing element securable to the holding part for securing the connection element in the connection element receptacle, further comprising a medical apparatus for parallel alignment of at least two medical instruments, defining an instrument longitudinal axis, for holding and manipulating a surgical fastening element, which fastening element comprises a fastening part and a holding part for a connection element, the holding part being mounted movably relative to the fastening part in a mounting position, which medical instruments have a distal end couplable to the fastening element, which apparatus comprises at least two coupling devices, each defining a coupling longitudinal axis, for temporary coupling with proximal ends of the at least two medical instruments, wherein the apparatus comprises a frame, wherein the coupling longitudinal axes of the at least two coupling devices are alignable parallel to one another, wherein in a mounting position the at least two coupling devices are held in such a way as to be movable relative to one another and on the frame and wherein in an alignment position they are held immovably relative to one another and on the frame, or a set of medical instruments as defined above.

Such a spine stabilisation system simply and reliably allows the alignment of vertebrae of a spine relative to one another.

FIG. 1 shows schematically, by way of example, part of a spine stabilisation system 10 comprising at least two surgical fastening elements and at least one connection element. FIG. 1 further shows three medical instruments 12 or a part thereof in the form of an outer sleeve 14, which may be coupled to the fastening element, not shown in FIG. 1, for example in the form of a bone screw, in particular a polyaxial pedicle screw, specifically with its distal ends 16. The spine stabilisation system 10 further comprises a medical apparatus 18 for orienting the longitudinal axes 20 of the instruments 12. The apparatus 18 further forms a part of a set of medical instruments 22 for implanting the spine stabilisation system 10, wherein the set of instruments 22 in particular comprises the instruments 12 and the apparatus 18.

The structure of the apparatus 18 is explained in detail below in conjunction with FIGS. 2 to 8.

The apparatus 18 comprises a frame designated overall with the reference sign 24 and formed from a plurality of parts. The exemplary embodiment illustrated schematically in FIGS. 2 to 5 comprises two frame parts 26 and 28. The first frame part 26 comprises two frame portions 30 and 32 which extend parallel to one another and form the frame longitudinal portions 34 and 36, which define frame longitudinal portion longitudinal axes 38 and 40 extending parallel to one another. The frame longitudinal portions 34 and 36 are connected at their one end via a frame cross-portion 42. A further frame cross-portion 44 is arranged mirror-symmetrical to the frame cross-portion 42 and connects the other free ends of the frame longitudinal portions 34 and 36, such that overall a closed, substantially rectangular frame 24 is formed.

The frame cross-portions 42 and 44 each define frame cross-portion longitudinal axes 46 and 48, which extend parallel to one another and transversely of, in particular perpendicularly to, the frame longitudinal portion longitudinal axes 38 and 40. Externally, the frame cross-portions 42 and 44 are curved substantially convexly away from the frame. Outer edges of the frame cross-portions are rounded, to minimise the risk of injury to a surgeon during use of the apparatus 18.

The two frame longitudinal portions 34 and 36 and the frame cross-portion 42 are made in one piece and form a basic unit of the frame 24. Free ends 50 of the frame longitudinal portions 34 and 36 are directed away from the frame cross-portion 42 and may be coupled with free ends 52 of the frame cross-portion 44 directed towards the frame cross-portion 42. The frame 24 thus defines an inner, free through opening 54 substantially elongatedly rectangular in shape.

Both frame longitudinal portions 34 and 36 comprise two rail parts 56 extending parallel to one another, which are mirror-symmetrical in form and each have a guide groove 58 open towards the other rail part 56. The free ends 50 of the rail parts 56 each have a blind hole 60, the longitudinal axis of which extends parallel to the frame longitudinal portion longitudinal axis 38. Cylindrical connecting pins 62, half of which projects substantially beyond the ends 50, are inserted into the blind holes 60 and form frame portion connecting projections 64 of a frame portion connection device 66 designated overall with reference sign 66. Two blind holes 68 are formed in each of the free ends 52 of the frame cross-portion 44. Said blind holes are open towards the ends 50 and define longitudinal axes extending parallel to the frame longitudinal portion longitudinal axes 38 and 40.

The connecting pins 62 are fastened either in blind hole 60 or in blind hole 68, for example by adhesive bonding or welding. The connecting pins 62, which are secured for example in the blind hole 60, together with the blind holes 68 form first and second interacting frame portion connection members 70 and 72 of the frame portion connection device 66, which are in force-locking and/or positive engagement with one another in a frame connection position, in which the parts forming the frame 24, i.e. for example the frame parts 26 and 28, are coupled together.

The blind holes 68 and the connecting pins 62 may be so dimensioned with regard to their internal diameter or external diameter respectively that the frame parts 26 and 28 are connected together in clamped manner. Optionally, latching elements or latching members may also be arranged or formed on the frame portion connection members 70 or 72, in a manner not shown, in order to configure the frame portion connection device 66 in the form of a latching and/or snap-fit connection device.

Overall, the frame 24 is of modular construction and can be enlarged by the use of frame portion extensions 74. The frame portion extensions 74 are of preferably identical construction and each comprise two rail parts 76, which, like the rail parts 56, have open guide grooves 78 facing one another.

Free ends 80 and 82 of the frame portion extension 74 extending parallel to the frame longitudinal portion longitudinal axes 38 and 40 have blind holes 84 and 86, which are configured in the same way as the blind holes 60 and define longitudinal axes extending parallel to the frame longitudinal portion longitudinal axes 38 and 40. Connecting pins 88 identical to the connecting pins 62 are in turn inserted into the blind holes 86 and held in clamped manner.

The configuration of the blind holes 84 and 86 and the arrangement of the connecting pins 88 in the blind holes 86 makes it possible to couple the frame part 28 with free ends of the frame portion extensions 74 from which the connecting pins 88 project. The frame part 28 with the frame portion extensions 74 may then be coupled to the frame part 26, specifically by inserting the connecting pins 62 into the blind holes 84. Overall, in this way the frame 24 may be enlarged as required.

In particular it is possible to provide not just two frame portion extensions 74 but also more, which may then be connected in a similar manner to one another and the frame parts 26 and 28. It is likewise possible to provide different length frame portion extensions 74 so as to be able to adapt the size of the frame 24 virtually as desired. In the frame 24 illustrated in FIGS. 6 to 8, the length of the frame portion extension 74 corresponds roughly to the length of the frame longitudinal portions 34 and 36.

The apparatus 18, as illustrated by way of example in FIGS. 1 to 8, further comprises three coupling devices 90, which each define a coupling longitudinal axis 92 and are configured to couple the instruments 12 in the region of the proximal ends 94 thereof. The coupling longitudinal axes 92 of the coupling devices 90 can be aligned parallel to one another.

Each coupling device 90 comprises two coupling members 96. Each coupling member 96 comprises a guide portion 98, a holding portion 100 and a connecting member 102 connecting the guide portion 98 and the holding portion 100.

The guide portion 98 substantially takes the form of a flat, square plate 104, which exhibits a height 106 which corresponds substantially to the distance between mutually facing groove faces 108 of the guide grooves 58 on the rail parts 56. The widths 110 and 112 of the guide grooves 58 on the frame longitudinal portions 34 and 36 are each somewhat greater than the thickness 114 of the guide portion 98.

The holding portion 100 takes the form of a portion of a hollow-cylindrical wall and has an instrument application face 116 facing the opposing holding portion 100 and conformed to an external contour of the medical instrument 12 in the region of the proximal end 94 thereof. The instrument application face 116 preferably takes the form of a hollow-cylindrical wall face portion 118. The guide portion 98, the connecting member 102 and the holding portion 100 are connected immovably to one another. The holding portion 100 is oriented in such a way relative to the guide portion 98 that the coupling longitudinal axes 92, which in particular form centre axes of the wall face portions 118, extend perpendicular to the frame longitudinal portion longitudinal axes 38 and 40 and perpendicular to the frame cross-portion longitudinal axes 46 and 48.

Movable connection of the coupling members 96 to the frame 24 is provided by a connection device 120 comprising first and second connection elements 122 and 124, wherein the first connection element 122 is arranged or formed on the frame 24 and the second connection element 124 is arranged or formed on the coupling member 96. The first connection element 122 takes the form of a connecting receptacle 126, which is formed by the two guide grooves 58 and 78 respectively.

The second connection element 124 takes the form of a connecting projection 128, specifically the form of the guide portion 98, which is translationally displaceable in the connecting receptacle 126 in the mounting position but not rotatable relative thereto. The connecting receptacle 126 forms part of the rail parts 56 or 76 respectively and comprises the guide grooves 58 or 78 respectively. The guide rails 130 are formed by the pairs of rail parts 56 of the frame longitudinal portions 34 and 36 or the frame portion extensions 74. Overall, the connection device 120 thus has two mutually parallel connecting receptacles 126.

Because the guide portions 98 are narrower than the guide grooves 58 and 78 are wide, the coupling members 96 may be moved relative to one another in a direction transverse to a longitudinal direction 132 defined by the first connection elements 122, i.e. parallel to the frame cross-portion longitudinal axes 46 and 48. Movement of the coupling members 96 towards one another is restricted in that stop faces 134, facing towards the holding portions 100, of the guide portions 98 strike against side faces 136, facing away from the holding portions 100, of the guide grooves 58 or 78 respectively.

Movement of the coupling members 96 away from one another is restricted in that a side face 138, facing away from the holding portion 100, of the guide portion 98 strikes against side faces 140, facing the holding portion 100, of the guide grooves 58 or 78 respectively. If the two mutually facing holding portions 100 of the two coupling members 96 forming a coupling device 90 are moved maximally towards one another, they assume the alignment position, which is illustrated schematically for example in FIG. 4. If they are deflected out of the alignment position, to enlarge the distance between the instrument application faces 116, the coupling device 90 is transferred from the alignment position into the mounting position, in which it is simply possible to guide the frame 24 for example via the ends 94 of the instruments 12, which have already been coupled with the fastening devices, not shown.

The coupling device 90 further comprises a locking device 142 for securing a position and/or alignment of the coupling members 96 in the alignment position. In the exemplary embodiment of an apparatus 18 shown schematically in FIGS. 1 to 8, said locking device takes the form of a clamping device 144 for clamped securing of the coupling members 96 in the alignment position on the frame 24.

The clamping device 144 comprises a clamping member 146 for clamped securing of the coupling members 96 in the alignment position on the frame 24. Each coupling member 96 has a clamping member 146 associated with it which takes the form of a spring element 148. In the apparatus 18, which is illustrated by way of example in FIGS. 1 to 8, this is formed by a helical spring 150 which serves as a compression member 152.

The clamping member 146 is supported on the one hand on the holding portion 100 and on the other hand on a side face 154 of the frame longitudinal portions 34 and 36 or of the frame portion extensions 74. In this way, in a basic position the coupling member 96 assumes the alignment position. The coupling member 96 may however be transferred from the alignment position into the mounting position against the action of the clamping member 146. In the process, the compression member 152 is compressed. Alternatively, the clamping member 146 surrounding the connecting member 102 could also be arranged in such a way that it is supported, surrounding the connecting member 102, on the one hand on the side face 136 and on the other hand on the stop face 134.

In the alignment position, the clamping member 146 forces the guide portion 98 against the side faces 136, such that it is virtually impossible or possible only with very great difficulty to displace the coupling members 96 in the connecting receptacle 126. If, however, the coupling members 96 are transferred into the mounting position, such that the guide portions 98 substantially lie neither on the side faces 136 nor on the side faces 140, then the coupling members 96 may be displaced parallel to the longitudinal direction 132 in the connecting receptacle 126. This makes it possible to position the coupling members 96 and thus the coupling devices 90 on the frame 24 in such a way that the instruments 12 may be secured in the coupling devices 90 in the desired manner, i.e. oriented parallel to one another, on the frame 24.

The number of coupling devices 90 arrangeable on the frame 24 may be simply modified by either removing or adding coupling members 96. This may be achieved most simply if for example the frame part 28 is separated from the frame part 26 and the ends 50 are exposed, such that further coupling members 96 may be inserted with their guide portions 98 into the connecting receptacles 126.

FIGS. 9 to 11 are schematic representations of a further exemplary embodiment of a medical apparatus 18. It virtually corresponds in structure to the exemplary embodiment of an apparatus 18 shown schematically in FIGS. 1 to 8, differing merely in that it does not comprise any clamping device 144, but rather a locking device 142 in the form of a blocking device 156.

The blocking device 156 comprises a blocking element 158, which takes the form of an elongate cuboidal strip 160 of a metal or a substantially non-resilient plastics material. The width 162 of the strip 160 corresponds to the height 106. The thickness 164 corresponds together with the thickness 114 of the guide portion 98 to a width 112 of the guide groove 58 or 78 respectively. This makes it possible to insert the blocking element 158 into the connecting receptacle 126 between the side face 136 of the guide portion 98 and the side faces 140 of the guide grooves 58 or 78 respectively.

If the strip 160 has been inserted into the connecting receptacle 126 in the described manner, as shown schematically in FIGS. 10 and 11, the coupling member 96 interacting with the blocking element 158 can no longer be moved relative to the other coupling member 96 of the coupling device 90. Thus the blocking device 156 blocks the coupling device 90 in the alignment position.

In order to transfer the coupling device 90 from the alignment position into the mounting position, the blocking element 158 is withdrawn from the connecting receptacle 126, such that the coupling members 96 may be displaced again parallel to the longitudinal direction 132 in the guide receptacle 100. Optionally, the coupling members 96 which are not in direct contact with the blocking element 156, as in the case of the exemplary embodiment of an apparatus 18 shown in FIGS. 1 to 8, may also comprise a clamping member 126.

FIGS. 12 to 15 are schematic representations of a further exemplary embodiment of a medical apparatus 18. The basic structure of the apparatus 18 corresponds with the structure of the apparatus 18 shown schematically in FIGS. 1 to 8. The only difference is in the configuration of the locking device 142, which although likewise constructed in the form of a clamping device 144, differs in the clamping members 146 interacting with the coupling members 98 guided in the guide grooves 58 or 78 respectively with the width 112.

The clamping members 146 do likewise take the form of spring elements 148, but the form of leaf springs 166 clamped to the guide portions 98. Each leaf spring 166 is mirror-symmetrical with regard to a plane of symmetry extending parallel to the frame cross-portion longitudinal axes 46 and 48. It has two free ends, which are bent round to form recesses 168, such that the recesses 168 face one another and grip round side faces of the guide portion 98 which face away from one another and are directed parallel to the longitudinal direction 132.

The leaf spring 166 is curved away from the side face 138 and lies with an outer face 170 facing convexly away from the guide portion 98 against the side faces 140 of the guide grooves 58 or 78 respectively. The leaf spring 166 in the form of a compression member 152 exerts a force away from the side face 140 on the guide portion 98 and in this way keeps the coupling member 96 biased towards the opposing coupling member 96. In other words, the clamping device 144 holds the coupling device 90 in the alignment position.

To transfer the coupling device 90 from the alignment position into the mounting position, the coupling member 90 may be displaced with the side face 138 towards the side face 140 against the action of the leaf spring 166. This then also allows displacement of the guide portion 98 and thus of the clamping member 96 parallel to the longitudinal direction 132 in the connecting receptacle 126. The coupling members 96 may thus, in the desired manner, be displaced to receive in particular proximal ends of the instruments 12 on the frame 24.

The coupling members 96 illustrated and described in FIGS. 12 to 15 may in principle also be exchanged for the coupling members 96 of the exemplary embodiment of a medical apparatus 18 illustrated schematically in FIGS. 1 to 8.

In particular, the frame 24 and also the other parts of the above-described exemplary embodiments of medical apparatuses 18 are preferably made from sterilisable, in particular steam-sterilisable materials. For reasons of stability, it is favourable for these materials to be metal or metal alloys. However, it is also feasible to use plastics which exhibit appropriate strengths for the purpose of the apparatuses 18.

The invention claimed is:

1. A medical apparatus for parallel alignment of at least two medical instruments, defining an instrument longitudinal axis, for holding and manipulating a surgical fastening element, which fastening element comprises a fastening part and a holding part for a connection element, the holding part being mounted movably relative to the fastening part in a mounting position, which medical instruments have a distal end couplable to the fastening element, which apparatus comprises at least two coupling devices, each defining a coupling longitudinal axis, for temporary coupling with proximal ends of the at least two medical instruments, wherein the apparatus comprises a frame, wherein the coupling longitudinal axes of the at least two coupling devices are alignable parallel to one another, wherein in a mounting position the at least two coupling devices are held in such a way as to be movable relative to one another and on the frame and wherein in an alignment position they are held immovably relative to one another and on the frame,
wherein each of the coupling devices comprises at least two coupling members, which in the mounting position are held so as to be movable relative to one another and on the frame and which in the alignment position are held immovably relative to one another and on the frame,
wherein the coupling device comprises a locking device for at least one of securing a position and alignment of the coupling members in the alignment position,
wherein the locking device comprises a clamping or blocking device for clamping securing of the coupling members on the frame in the alignment position or for blocking movement thereof relative to one another, and
wherein the clamping device comprises at least one clamping member for clamping securing of the coupling members on the frame in the alignment position, wherein the at least one clamping member takes the form of a spring element.

2. An apparatus according to claim 1, wherein each coupling member has an instrument application face, which is conformed to an external contour of the medical instrument in the region of the proximal end thereof.

3. An apparatus according to claim 1, wherein the frame comprises a first frame portion and a second frame portion, which extend parallel to one another.

4. An apparatus according to claim 3, wherein the frame comprises at least two frame cross-portions, which extend parallel or substantially parallel to one another, wherein the first frame portion and the second frame portion form frame longitudinal portions, and wherein the at least two frame cross-portions connect together the frame longitudinal portions.

5. An apparatus according to claim 1, wherein the frame is of modular construction and comprises at least one frame portion extension for extending the first and second frame portions and wherein the at least one frame portion extension is detachably connectable to at least one of the first and second frame portion.

6. An apparatus according to claim 1, further comprising a frame portion connection device for detachable connection of parts forming the frame.

7. An apparatus according to claim 6, wherein the frame portion connection device comprises first and second interacting frame portion connection members, which are engaged in at least one of force- and positively-locking manner with one another in a frame connection position.

8. An apparatus according to claim 7, wherein the first and second interacting frame portion connection members are arranged or formed on at least one of a frame portion, a frame longitudinal portion, a frame cross-portion and a frame portion extension.

9. An apparatus according to claim 1, further comprising a connection device for movable connection of the coupling members with the frame.

10. An apparatus according to claim 9, wherein the connection device comprises at least one first connection element and at least one second connection element interacting with the at least one first connection element, wherein the frame comprises the at least one first connection element and wherein the at least one second connection element is arranged or formed on the coupling member.

11. An apparatus according to claim 10, wherein the at least one first connection element takes the form of a connection receptacle and wherein the at least one second connection element takes the form of a connecting projection.

12. An apparatus according to claim 11, wherein the connecting receptacle is part of a guide rail or guide groove.

13. An apparatus according to claim 1, wherein the at least two coupling members defining a coupling device are movable relative to one another in a direction transverse to a longitudinal direction defined by the at least one first connection element away from one another on changeover from the alignment position to the mounting position and towards one another on changeover from the mounting position to the alignment position.

14. An apparatus according to claim 1, wherein at least one of the coupling members has a guide portion, a holding portion and a connecting member connecting the guide portion and the holding portion.

15. An apparatus according to claim 14 comprising a connection device, wherein the connection device comprises at least one first connection element and at least one second connection element interacting with the at least one first connection element, and wherein the guide portion at least one of is or comprises the at least one second connection element and is configured for non-rotatable displacement on the at least one first connection element.

16. An apparatus according to claim 15, wherein the at least one first connection element takes the form of a connecting receptacle, and wherein the clamping member is supported on the one hand on the holding portion and on the other hand on the connecting receptacle or on the one hand on the connecting receptacle and on the other hand on the guide portion.

17. A spine stabilization system comprising: at least two surgical fastening elements; at least one connection element; and the medical apparatus of claim 1.

18. A set of medical instruments for implanting a spine stabilisation system, which set of medical instruments comprises at least two medical instruments for holding and manipulating a surgical fastening element, which fastening element comprises a fastening part and a holding part for a connection element, the holding part being mounted movably relative to the fastening part in a mounting position, which medical instruments have a proximal end and a distal end couplable to the fastening element, further comprising a medical apparatus for parallel alignment of said at least two medical instruments, defining an instrument longitudinal axis, which apparatus comprises at least two coupling devices, each defining a coupling longitudinal axis, for temporary coupling with proximal ends of the at least two medical instruments, wherein the apparatus comprises a frame, wherein the coupling longitudinal axes of the at least two coupling devices are alignable parallel to one another, wherein in a mounting position the at least two coupling devices are held in such a way as to be movable relative to one another and on the frame and wherein in an alignment position they are held immovably relative to one another and on the frame, wherein each of the coupling devices comprises at least two coupling members, which in the mounting position are held so as to be movable relative to one another and on the frame and which in the alignment position are held immovably relative to one another and on the frame, wherein the coupling device comprises a locking device for at least one of securing a position and alignment of the coupling members in the alignment position, wherein the locking device comprises a clamping or blocking device for clamping securing of the coupling members on the frame in the alignment position or for blocking movement thereof relative to one another, and wherein the clamping device comprises at least one clamping member for clamping securing of the coupling members on the frame in the alignment position, wherein the at least one clamping member takes the form of a spring element.

19. A medical apparatus for parallel alignment of at least two medical instruments, defining an instrument longitudinal axis, for holding and manipulating a surgical fastening element, which fastening element comprises a fastening part and a holding part for a connection element, the holding part being mounted movably relative to the fastening part in a mounting position, which medical instruments have a distal end couplable to the fastening element, which apparatus comprises at least two coupling devices, each defining a coupling longitudinal axis, for temporary coupling with proximal ends of the at least two medical instruments, wherein the apparatus comprises a frame, wherein the coupling longitudinal axes of the at least two coupling devices are alignable parallel to one another, wherein in a mounting position the at least two coupling devices are held in such a way as to be movable relative to one another and on the frame and wherein in an alignment position they are held immovably relative to one another and on the frame;

wherein each of the coupling devices comprises at least two coupling members, which in the mounting position are held so as to be movable relative to one another and on the frame and which in the alignment position are held immovably relative to one another and on the frame;

wherein at least one of the coupling members has a guide portion, a holding portion and a connecting member connecting the guide portion and the holding portion;

wherein a connection device comprises at least one first connection element and at least one second connection element interacting with the at least one first connection element;

wherein either:
  a) the guide portion at least one of is or comprises the second connection element and is configured for non-rotatable displacement on at least one first connection element, or
  b) the at least one first connection element takes the form of a connection receptacle; and wherein the clamping member is supported on the one hand on the holding portion and on the other hand on the connecting receptacle or on the one hand on the connecting receptacle and on the other hand on the guide portion.

20. An apparatus according to claim 19, wherein the coupling device comprises a locking device for at least one of securing a position and alignment of the coupling members in the alignment position.

21. An apparatus according to claim 20, wherein the locking device comprises a clamping or blocking device for clamping securing of the coupling members on the frame in the alignment position or for blocking movement thereof relative to one another.

22. An apparatus according to claim 21, wherein the clamping device comprises at least one clamping member for clamping securing of the coupling members on the frame in the alignment position.

23. An apparatus according to claim 22, wherein at least one coupling member of each coupling device is transferable from the alignment position into the mounting position against the action of the clamping member.

24. An apparatus according to claim 22, wherein just one of the at least two coupling members of a coupling device comprises a clamping member.

* * * * *